US005690529A

United States Patent [19]

Oberpriller et al.

[11] Patent Number: 5,690,529
[45] Date of Patent: Nov. 25, 1997

[54] ADSORBER MATERIAL, APPARATUS AND PROCESS FOR CONCENTRATING AND RECOVERING TRACE MATERIALS FROM THE GASEOUS PHASE

[75] Inventors: Helmut Oberpriller, Feldkirchen; Reinhold Hilpert, Moorenweis; Florian Binder, Traunstein; Josef Ritter, Munich; Harald Ertl, Gelting; Rolf Lerch, Ilvesheim; Reiner Schlipfenbacher, Bad Durkheim; Ludwig Angermaier, Bichl; Christian Klein, Weilheim, all of Germany

[73] Assignees: Securetec GmbH, Vagen; Boehringer Mannheim GmbH, Mannheim, both of Germany

[21] Appl. No.: 748,618

[22] Filed: Nov. 13, 1996

Related U.S. Application Data

[63] Continuation of Ser. No. 380,423, Jan. 27, 1995, abandoned.

[30] Foreign Application Priority Data

Jan. 27, 1994 [DE] Germany .......................... 44 02 377.4

[51] Int. Cl.$^6$ .......................... G01N 13/00; D04H 3/00; D04H 3/12
[52] U.S. Cl. .......................... 442/414; 442/415; 442/416; 73/31.07; 73/31.01; 96/4; 95/273
[58] Field of Search .......................... 442/414, 415, 442/416; 73/31.07, 31.01; 96/4; 95/273

[56] References Cited

U.S. PATENT DOCUMENTS

| | | | |
|---|---|---|---|
| 3,855,046 | 12/1974 | Hansen et al. | 428/198 |
| 4,100,324 | 7/1978 | Andersen et al. | 428/288 |
| 4,512,245 | 4/1985 | Goldman | 55/115.4 |
| 4,541,268 | 9/1985 | Odernheimer . | |
| 4,705,712 | 11/1987 | Cashaw et al. | 428/152 |
| 4,753,834 | 6/1988 | Braun et al. | 428/74 |
| 5,082,473 | 1/1992 | Keefer | 55/25 |
| 5,401,594 | 3/1995 | Schwobel et al. | 429/142 |

FOREIGN PATENT DOCUMENTS

| | | |
|---|---|---|
| 4121493 | 1/1993 | Germany . |
| 3-274460 | 5/1991 | Japan . |

OTHER PUBLICATIONS

Kovar, et al., "IMS and Preconcentration", International Symposium for Drug Detection, Wiesbaden 1991, Bundeskriminalamt.

Draeger, *Probenahme-Handbuch*, Draegerwerk Aktiengesellschaft, 1991.

*Measurement of Gaseous Emissions; Gaschromatographic Determination of Organic Compounds—Sampling by Enrichment Thermal Desorption*, VDI-Handbuch Reinhaltung der Luft, 3482.

*Gaseous Emission Measurement; Gas Chromatographic Determination of Organic Compounds—Fundamentals*, VDI-Handbuch Reinhaltung der Luft, 2457.

*Empfohlene Analysenverfahren fuer Arbeitsplatzmessungen*, Schriftenreihe der Bundesanstalt für Arbeitsschutz, Gefährliche Arbeitsstoffe, GA 13.

Matz, "Rauschgift-Detektion mit dem Mobilen Massenspektrometer", International Symposium for Drug Detection, Wiesbaden 1991, Bundeskriminalmt.

Fine, et al., "Detection of Cocaine, Heroin and Methamphetamines by Means of Very High Speed Chromatography Coupled to a Chemiluminescence Detector", International Symposium Drug Detection, Wiesbaden 1991, Bundeskriminalamt.

Zaromb, et al., "Detection of Airborne Cocaine and Heroin by High-Throughput Liquid-Absorption Preconcentration and Liquid Chromatography-Electrochemical Detection", *J. Chromatogr.*, vol. 643, pp. 107–115 (1993).

Lawrence, et al., "Determination of Amphetamine, Cocaine, and Heroin Vapour Pressures Using a Dynamic Gas Blending System and Gas Chromatographic Analysis", *Can. J. Chem.*, vol. 62, pp. 1886–1888, (1984).

*Primary Examiner*—Kathleen Choi
*Attorney, Agent, or Firm*—Evenson, McKeown, Edwards & Lenahan P.L.L.C.

[57] ABSTRACT

An adsorber material for collecting, concentrating and/or recovering gaseous and/or particle-shaped trace substances from an air or gas flow, in which the adsorber material is composed of fibrous elements made of natural and/or synthetic, organic, textile fibers which are worked into a nonwoven web having a planar geometry, the nonwoven web having a thickness of between 100 μm and 2 mm and a weight per unit area of between 20 and 200 g/m$^2$. Preferably the fibers have a fiber size between 1 and 10 dtex and are composed of cellulose and/or polyester, and if desired, the fibers may be provided with a binding agent and/or a moisture resistance agent. In preferred embodiments the nonwoven adsorber web is a fiber mixture of 80 parts polyester fibers, 20 parts viscose rayon staple fibers, and 20 parts polyvinyl alcohol fibers or a fiber mixture of 50 parts viscose rayon staple fibers and 50 parts linters, which are provided with an epichlorohydrin resin binder. The adsorber webs can be used to detect gaseous or particulate trace contaminants in air or another gas stream.

13 Claims, 1 Drawing Sheet

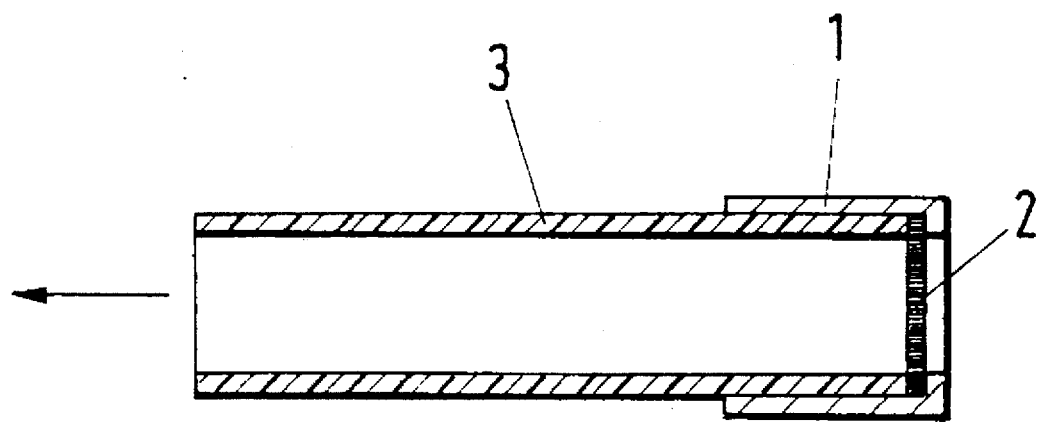

ADSORBER MATERIAL, APPARATUS AND PROCESS FOR CONCENTRATING AND RECOVERING TRACE MATERIALS FROM THE GASEOUS PHASE

This application is a continuation of application Ser. No. 08/380,423 filed on Jan. 27, 1995, now abandoned.

BACKGROUND OF THE INVENTION

The concentration and recovery of trace materials from a gaseous phase is a task which is important in many fields of application. Thus, for example, when combatting drug-related crimes, it is necessary to concentrate drug molecules or drug particles or drugs attached to particles which are freely present in the gaseous phase in order to prove their presence by means of suitable processes. [BKA(ed.): Internationales Symposium Detektion von Rauschgift (International Symposium for the Detection of Narcotics), Wiesbaden 1991]. Similar problems also occur, for example, in monitoring workplaces and in environmental analysis.

In the prior art there are a number of adsorber materials, apparatuses and processes currently used for this purpose which, however, have specific disadvantages.

Adsorption devices in the form of small tubes which are filled with adsorber materials, such as activated carbon or silica gel, are generally known [Draeger Co.: Probenahme-Handbuch (Sampling Manual), 1st Edition, 1991]. Disadvantages of such devices include limited gas permeability (typically within the range of from 200 to 400 ml/min.), a relatively large volume of the adsorber bed which requires large elution volumes, and the fact that some substances (particularly non-volatile trace materials such as cocaine) bind very strongly to these materials and are difficult to desorb again.

It is also known to use adsorber modules in the form of small tubes filled, for example, with quartz glass for concentration and subsequent thermal desorption [see VDI-Richtlinie (VDI-Guideline) 3482). In this case also, only comparatively low flow rates can be achieved and the adsorber bed has a relatively large volume. Thermal desorption generally has the further disadvantage that after the thermal desorption, the concentrated trace material again exists in the gaseous phase which is disadvantageous for subsequent steps, for example, for detection by means of immunological procedures.

Another known process is to concentrate trace materials from the gaseous phase by passing a sample gas through a liquid suitable for dissolving the trace material to be concentrated in a glass vessel [e.g. Impinger, cf. VDI-Richtlinie (VDI-Guideline) 3482]. In this case it is a disadvantage that relatively large volumes of solvent must be used so that comparatively large gas volumes must be collected in order to achieve significant enrichment factors in the liquid trap (normally >100 l). Another problem in this type of concentration procedure is the evaporation of the solvent during the sampling operation.

Combination processes are also known with different solid adsorber materials or with solid adsorber materials and solvent traps [Bundesanstalt fuer Arbeitsschutz (Federal Office for the Protection of Labor) ed.: "Empfohlene Analysenverfahren zur Arbeitsplatzmessung (Recommended Analysis Procedures for Measuring Workplaces)," 1991]. In addition to the above-mentioned disadvantages, a particular problem in this case is high apparatus cost.

Another known process is the use of metallic mesh (e.g., nickel, gold) which optionally may be additionally coated with organic phases [Matz, G.: "Rauschgift-Detektion mit dem mobilen Massenspektrometer (Detection of Narcotics With the Mobile Mass Spectrometer)," BKA-Symposium "Detektion yon Rauschgift (Detection of Narcotics)," Wiesbaden, 1991; Fine, D. H., et al.: "Detection of Cocaine, Heroin and Methamphetamine by Means of Very High Speed Chromatography Coupled to a Chemiluminescence Detector," ibid.]. Such adsorber materials and processes are used primarily if a subsequent analysis is to be carried out by gas chromatography and/or mass spectrometry. These materials and processes are suitable primarily for concentrating trace particles or trace materials which are bound to particles. Nothing is known concerning their suitability for adsorption of gaseous trace materials. Since these materials are comparatively expensive, it only makes sense to use them if they can be used several times. This has the result that in analytical applications, there is a risk of overloading and therefore of loss of the analyzed material.

Published German Patent Application No. DE-OS 4,121, 493 describes an arrangement for detecting harmful substances in the gaseous phase, in which the substances are detected by means of immunological reactions, and the gaseous phase to be examined is diffused or actively sucked through a membrane-type carrier. A disadvantage of such adsorption materials and processes is the low gas permeability of such membranes which requires a longer time for sampling and a higher apparatus cost in order to achieve a significant gas flow.

In order to concentrate trace materials (in this case, methamphetamine), Published Japanese Patent Application No. JP-A 3-274,460 also uses a membrane material which permits a gas flow of 1 l/min. with pore diameters of 0.45 µm and a membrane thickness of 100 µm over a surface of approximately 7 cm$^2$. Also in this it is a disadvantage that the gas flow rates are comparatively low which results in a high time requirement in order to sample a practical gas volume.

Zaromb, et al. (*Journal of Chromatography* Vol. 643, Pgs. 107–115 (1993) describes a concentrating device which is suitable for large gas volumes (550–700 l/min). In this case, the gaseous phase to be concentrated is brought in contact with an aqueous adsorption medium in a tube to which the aqueous adsorption medium containing additives is continuously fed, and thus trace substances present in the gaseous phase are concentrated in the aqueous adsorption medium. The authors describe sampling times between 10 and 60 minutes which corresponds to total volumes of the sampled gas between approximately 5,000 and 42,000 l. Such large gas sample volumes have the disadvantage that they are no longer relevant for many analytical problem situations. Thus, for example, when using such large sampling volumes in examining suspicious pieces of luggage for illegal drugs, the sample which is taken in is predominantly ambient air which is of no significance with respect to the solution of the problem. Another disadvantage of the above-described process is the high apparatus cost.

In summary, it may be stated that all adsorber materials and/or processes known in the prior art for concentrating and/or recovering trace materials present in the gaseous phase have one or more of the following disadvantages:

long time requirements high apparatus costs low gas permeability require very high gas volumes uncertain suitability for gaseous trace materials risk of overloading and consequent loss of material poor eluability of the adsorbed trace material require relatively large elution volumes.

SUMMARY OF THE INVENTION

It is therefore the object of the present invention to eliminate the above-described disadvantages. This and other objects of the invention are achieved by providing an adsorber material for concentrating and recovering trace materials from a gas stream, wherein the adsorber material is a planar, nonwoven web of natural or synthetic textile fibers, the web having a thickness of from 100 μm to 2 mm and having a weight per unit area of from 20 to 200 g/m².

BRIEF DESCRIPTION OF THE DRAWING

The accompanying drawing FIGURE is a sectional representation of a support for a nonwoven web adsorber according to the invention.

DETAILED DESCRIPTION OF PREFERRED EMBODIMENTS

In the adsorber material of the invention, the fibers are composed of cellulose (linters/rayon staple fibers/viscose) and/or of polymeric fibers composed of polyester. An organic binding agent, which contains hydroxyl groups and/or ester groups (e.g. polyvinyl alcohol or epichlorohydrin resin) may be used for the nonwoven web.

Preferably, cellulose fibers, such as viscose rayon staple fibers, cellulose and linters, are used. The term "viscose rayon fibers" refers to a material obtained by alkalizing cellulose to form alkali cellulose, subsequently treating the alkali cellulose with carbon bisulfide to form cellulose xanthates, dissolving the cellulose xanthates in lye and spinning the solution into a viscose (rayon) filament yarn. Cellulose can be obtained by complete chemical breakdown of cellulose-containing materials and subsequent bleaching. The term "linters" refers to short, non-spinnable cotton fibers which are obtained from cotton seeds.

In general, the fibers have a fiber size between 1 and 10 dtex.

The cellulose fibers preferably have a fiber size (fiber diameter) of from 1.7 to 4.5 dtex and have lengths of from 3 to 12 mm.

Particularly preferred polyester fibers are fibers with a specific weight of approximately 1.17 g/cm³, a cut length of 3 to 6 mm and a fiber size (fiber diameter) of from 1.7 to 3.3 dtex.

As a further component, the nonwoven webs may contain an organic binding agent which has OH-groups and/or ester groups. Polyvinyl alcohol and epichlorohydrin resins are preferably used for this purpose. Polyvinyl alcohol is preferably used in the form of a fiber material with a cut length of 4 mm and a specific weight of from 1.26 to 1.30 g/cm³.

From these constituents and deionized water, a nonwoven web is produced on an oblique-wire machine in accordance with to the conventional process used in manufacturing paper. No further additives or auxiliary agents are required.

Preferred embodiments include:

a) a nonwoven web formed from a mixture of rayon staple fibers and linters in a 1:1 ratio (hereinafter referred to as VLS 352), and b) a nonwoven web composed of 80 parts polyester fibers and 20 parts rayon staple fibers (hereinafter referred to as VLS 317).

At a thickness of between 100 μm and 2 mn and a weight per unit area of between 20 and 200 g/m², the nonwoven webs of the invention are distinguished in comparison to conventional filter papers in that they achieve much higher gas permeability values while simultaneously exhibiting good adsorption performance. During testing of the gas permeability, 400 cm³ of air per second are blown through a 10 cm² test surface and the air resistance is measured in mbar. In the case of VLS 352, the resistance is 4.5 mbar; in the case of VLS 317, the resistance is 1.0 mbar. Conventional filter papers yield clearly higher values of approximately 16.0 mbar.

Using another test method, comparative measurements were also carried out with membrane-like adsorber materials as described in published Japanese Patent Application No. JP 3-274,460. In this case, volume flows in the range from 1 to 10 liters per minute and cm² of adsorber material are generated by means of a vacuum pump and the resulting pressure drop above the adsorber material is determined in mbar. The results of this series of tests are listed in the following table:

| Material | Volume Flow (liters min⁻¹ cm⁻²) | Pressure Drop (mbar) |
| --- | --- | --- |
| VLS 352 | 6 | 160 |
| VLS 352 | 7.4 | 280 |
| VLS 317 | G | 160 |
| VLS 317 | 7.4 | 285 |

It can be seen that with the adsorber webs of the invention, only relatively small pressure drops arise at comparatively high volume flows. With membrane-type comparison samples, clearly much higher pressure drops are observed at very small volume flows.

The nonwoven web-type adsorber materials of the invention are fastened in a suitable support in such a manner that it is possible for the sample gas containing the trace substances to be absorbed to have free access to the nonwoven adsorber web. The surfaces of the support for the adsorber material which come in contact with the sample gas before the actual adsorber material must thereby be designed to be as small as possible in order to prevent undesirable adsorption on these surfaces. Normally the surface area of the nonwoven adsorber web will be chosen between 0.1 and 100 cm², preferably between 0.5 and 20 cm² and particularly preferably between 1 and 5 cm². The sample gas which contains the trace substance or substances to be adsorbed is then forces through the nonwoven-type adsorber material, whereupon the trace material(s) to be concentrated are adsorbed on the nonwoven adsorber material. The gas flow preferably is controlled by means of an adjustable vacuum pump which is arranged downstream of the support for the adsorber material. Advantageously, the flow rate is adjusted to be between 1 ml/min and 100 liters/min, preferably between 100 ml/min and 20 liters/min and particularly preferably between 500 ml/min and 10 liters/min. For subsequent recovery and further use of trace materials concentrated from the gas phase (e.g. for analytical purposes), the trace materials are eluted from the adsorber material with suitable solvents and/or optionally they may be thermally desorbed. Suitable eluting agents include aqueous solutions, such as buffer substances dissolved in water, to which additional additives, such as detergents, may also be added, as well as organic solvents. The concentrated trace material may be eluted by chromatography (i.e., the elution agent which is used may move through the adsorber material due to capillary action) as well as by actively rinsing the adsorber material, for example, by means of a liquid pump.

Elution agent volumes between 1 μl and 1,000 ml, preferably between 10 μl and 10 ml, and particularly preferably between 50 μl and 1 ml, may be used advantageously.

In summary, the adsorber materials according to the invention are distinguished in that, with comparatively low apparatus cost, a comparatively low pressure drop across the adsorber material (which at the aforementioned flow rates typically lies between 50 and 500 mbar) and comparatively small dimensions of the adsorber material, sample gas flow rates may be achieved which cover a range which is relevant for many applications, particularly analytical applications. Furthermore, the adsorber materials according to the invention are distinguished by the fact that, again with comparatively small dimensions of the adsorber material, particularly with a nonwoven adsorber web having a comparatively small thickness, and with sample gas flow rates which are comparatively high, trace substances which are present in gaseous form as well as in the form of particles or are attached to particles are substantially quantitatively (i.e. almost completely) retained. Another advantage of the adsorber materials according to the invention is the fact that the concentrated trace materials can be almost quantitatively eluted again by means of comparatively simple solvents, such as buffers, which are also very compatible with, for example, subsequent immunological detection processes. Because of the small dimensions of the adsorber materials, comparatively small volumes of elution agent may be used for the elution which represents another advantage, particularly with respect to the achievable concentration factor. Finally, because of their comparatively low cost, the adsorber materials according to the invention may be utilized in adsorber modules for one-time use, so that no cross-contamination problems between individual samples will occur, which is particularly advantageous in analytical applications.

In the following, the invention will be described in further detail with reference to illustrative preferred embodiments.

EXAMPLE 1

Accumulation of Gaseous Cocaine at Saturation Concentration

A nonwoven web produced which was composed of 80 parts polyester fibers having a fiber size of 3.3 dtex and a fiber length of 4 mm, 20 parts rayon staple fibers having a fiber size of 1.7 dtex and a cut length of 3 mm, and 20 parts polyvinyl alcohol fibers having a cut length of 4 mm. The fiber materials polyester, rayon staple fiber and polyvinyl alcohol, in deionized water at a material density of 0.3%, were beaten open and separated in mixing vats. The fiber material was subsequently pumped onto a rotary sieve. While the fiber mixture is dewatered or the water is sucked off by a vacuum, the fibers orient themselves on the side of the sieve and are contact dried as a nonwoven web with a dry matter content of approximately 20% by means of drying cylinders. The weight per unit area of a nonwoven adsorber web produced in this manner amounted to 80 g/m$^2$; the thickness was 320 μm.

Round disks having a diameter of 14 mm were punched out of the above and were inserted in a support as shown in FIG. 1. This consists essentially of a cylindrical holder 1, which clamps the nonwoven web 2 against the axial end face of a plastic (synthetic resin) tube 3. The rear end of the plastic tube is connected with a vacuum pump.

The cocaine gas phase was prepared by means of a test gas stand in which nitrogen gas at a given temperature is conducted through a likewise temperature controlled base layer of solid cocaine (free base). The entire gas flow through the test gas stand takes place under isothermal conditions in order to ensure a uniform gas quality. The presence of a uniform gas quality at the outlet of the test gas stand is determined by an instrumental reference analysis [introduction of the test gas into several successively connected solvent traps; analysis by gas chromatograph or mass spectrometer (GC/MS)]. At a temperature of 20°, a cocaine concentration of approximately 2 ng/l, which corresponds to the theoretically expected saturation concentration of cocaine at this temperature, can be produced in a reproducible manner by means of the described test gas stand (Lawrence, at l., Can. J. Chem. 82, 1984).

The support with the inserted adsorber material is connected with a flow-controlled vacuum pump. A flow of 5 liters/min is adjusted, the flow being additionally monitored by means of a flow meter (Rotameter) inserted into the gas channel. A pressure drop of approximately 140 mbar thereby arose across the adsorber material. At the adjusted flow rate, the adsorber material was contacted for 2 min by the cocaine-saturated gas phase at the outlet of the test gas stand. The total contact amount thus corresponded to approximately 20 ng cocaine/adsorber web. Then, the adsorber material was removed from the support by means of forceps and was transferred to an Eppendorf reaction vessel. Here, the nonwoven web was eluted with 200 μl of a mixture of cyclohexane and ethanol (1:1). The amount of cocaine in the eluate was quantitatively determined by means of GC/MS. In each case at least five parallel samples were taken for each test series.

In a parallel test series, the elution was carried out by means of an aqueous buffer (50 mmole/liter HEPES, 0.9% NaCl, 0.05% Tween 20, pH 6.8). In this case the amount of cocaine in the eluate was determined by means of a cocaine-specific ELISA.

The individual results are listed in the following table:

| Sample | ng Cocaine total/Adsorber Web |
|---|---|
| a) Elution with cyclohexane/ethanol, Analysis with GC/MS | |
| 1 | 18.2 |
| 2 | 22.1 |
| 3 | 20.9 |
| 4 | 19.0 |
| 5 | 18.8 |
| b) Elution with Buffer, Analysis with ELISA | |
| 1 | 19.8 |
| 2 | 19.3 |
| 3 | 20.9 |
| 4 | 19.4 |
| 5 | 21.2 |

The results show that at a cocaine concentration in the gas phase which corresponds to the saturation concentration, the gaseous cocaine is both quantitatively retained on the adsorber web and also quantitatively elutable from the adsorber web by means of the aqueous buffer solution.

EXAMPLE 2

Accumulation of Gaseous Cocaine at a Concentration Below the Saturation Concentration An adsorber web was produced as described in Example 1 which had the following composition:
Rayon fiber: fiber size 1.7 dtex, cut length 3 50 parts
Linters: Type 3386, Temming Co. 50 parts Epichlorohydrin resin (12.5% solids) 3 parts A nonwoven web produced in this manner has a weight per unit area of 100 g/m² at a thickness of approximately 400 μm.

A dilution of the sample gas described in Example 1 produced by dilution with nitrogen in an additional dilution path was used as the sample gas. The monitoring of the actual cocaine concentrations present in the respective diluted gas phases was carried out by contacting adsorber tubes filled with silica glass with a defined amount of sample gas, thermally desorbing the adsorbed cocaine in a thermodesorption unit, and quantitative analysis by means of a directly connected GC/MS. Dilutions were produced which corresponded to 10% (corresponding to 200 pg/liter) or 1% (corresponding to 20 pg/liter) of the saturation concentration of cocaine at 20° C. The cocaine-laden filters were eluted exclusively by means of elution buffers; the amount of cocaine in the eluate was detected exclusively by means of the cocaine-specific ELISA. All other conditions corresponded to those described in Example 1.

Result: The recovery was 2(±0.2) ng absolute per adsorber web when contacted with 10 liters of a cocaine-containing gaseous phase with a cocaine concentration of 200 pg/l, or 200(±35) pg absolute per adsorber web when contacted by 10 liters of a cocaine-containing gaseous phase with a cocaine concentration of 20 pg/liter.

The result shows that very low absolute amounts of cocaine, as are present at cocaine concentrations in the gaseous phase far below the saturation concentration, also are retained in a reproducible manner on the nonwoven adsorber web and that it is possible to quantitatively elute them by means of an aqueous buffer solution.

EXAMPLE 3

Retention of Particulate Cocaine

The nonwoven adsorber web, the support, the flow rates, the elution and the analysis corresponded to those of Example 2. However, in contrast to Example 2, the nonwoven adsorber web was not contacted by a sample gas from a test gas stand; instead the sample was taken a distance of 1 cm above a polyethylene surface which had previously been contaminated with a powdery mixture of 1 part cocaine in 1,000 parts lactose, 5 mg of this mixture having been distributed over a surface area of 200 cm². During the sampling, a 5 liter per minute stream of compressed air was additionally blown against the surface from a distance of approximately 1 cm out of an approximately 1 mm diameter nozzle in order to promote distribution of the particulate contamination.

Result: Absolute quantities of >20 ng cocaine were detected on all filters contacted in this manner. The results show that cocaine which exists in the form of particles suspended in the gaseous phase also is retained by the nonwoven adsorber web according to the invention.

The foregoing description and examples have been set forth merely to illustrate the invention and are not intended to be limiting. Since modifications of the disclosed embodiments incorporating the spirit and substance of the invention may occur to persons skilled in the art, the invention should be construed to include everything within the scope of the appended claims and equivalents thereof.

What is claimed is:

1. An apparatus capable of detecting trace materials in a gas, the improvement comprising an adsorber material for concentrating and recovering trace materials from a gas stream, wherein said adsorber material is a planar, nonwoven web of natural or synthetic textile fibers, said web having a thickness of from 100 μm to 2 mm and having a weight per unit area of from 20 to 200 g/m².

2. An adsorber material according to claim 1, wherein said trace material is a gaseous material.

3. An adsorber material according to claim 1, wherein said trace material is a particulate material suspended in said gas stream.

4. An adsorber material according to claim 1, wherein said gas stream is an air stream.

5. An adsorber material according to claim 1, wherein said fibers have a fiber size between 1 and 10 dtex.

6. An adsorber material according to claim 1, wherein said fibers are cellulose fibers.

7. An adsorber material according to claim 1, wherein said fibers are polyester fibers.

8. An adsorber material according to claim 1, wherein said fibers consist of a mixture of cellulose fibers and polyester fibers.

9. An adsorber material according to claim 1, wherein said fibers consist of a mixture of 80 parts polyester fibers, 20 parts viscose staple fibers and 20 parts polyvinyl alcohol fibers.

10. An adsorber material according to claim 1, wherein said fibers are bonded by a binding agent.

11. An adsorber material according to claim 1, wherein said fibers are treated with an agent which enhances resistance of the nonwoven web to moisture.

12. An adsorber material according to claim 1, wherein said nonwoven web consists of a fiber mixture of 50 parts rayon staple fibers and 50 parts linters, and said fiber mixture is bonded with an epichlorohydrin resin binding agent.

13. A process for concentrating and recovering trace materials from a gas comprising passing a stream of the gas through an adsorber material consisting of a planar, nonwoven web of natural or synthetic textile fibers, said web having a thickness of from 100 μm to 2 mm and having a weight per unit area of from 20 to 200 g/m².

* * * * *